United States Patent
Smith et al.

(10) Patent No.: US 8,291,780 B2
(45) Date of Patent: Oct. 23, 2012

(54) SENSOR FINGER MODULE FOR A PIPELINE INSPECTION TOOL

(75) Inventors: Derek R. Smith, Stocksfield (GB); Eduardo Boada, North Shields (GB); Gary Brayson, Tynemouth (GB)

(73) Assignee: PII Limited, Cramlington (GB)

( * ) Notice: Subject to any disclaimer, the term of this patent is extended or adjusted under 35 U.S.C. 154(b) by 1015 days.

(21) Appl. No.: 11/571,458

(22) PCT Filed: Jun. 30, 2005

(86) PCT No.: PCT/GB2005/002561
§ 371 (c)(1),
(2), (4) Date: Jun. 29, 2007

(87) PCT Pub. No.: WO2006/003392
PCT Pub. Date: Jan. 12, 2006

(65) Prior Publication Data
US 2008/0011063 A1    Jan. 17, 2008

(30) Foreign Application Priority Data
Jul. 1, 2004  (GB) .................................. 0414781.5

(51) Int. Cl.
*G01M 99/00* (2011.11)
(52) U.S. Cl. ...................... 73/865.8; 324/220
(58) Field of Classification Search ............ 73/40.5, 73/623, 865.8; 324/220
See application file for complete search history.

(56) References Cited

U.S. PATENT DOCUMENTS

| | | | |
|---|---|---|---|
| 4,105,972 A | 8/1978 | Smith | |
| 4,123,847 A * | 11/1978 | Bosselaar et al. | 33/544.3 |
| 4,393,698 A | 7/1983 | Pietzsh | |
| 4,457,073 A | 7/1984 | Payne | |
| 4,924,595 A * | 5/1990 | Wamser et al. | 33/542 |
| 5,641,897 A * | 6/1997 | Schuman | 73/105 |
| 6,012,337 A | 1/2000 | Hodge | |
| 6,196,075 B1 * | 3/2001 | Comello et al. | 73/865.8 |
| 6,376,784 B1 * | 4/2002 | Morinaka | 177/121 |
| 6,640,655 B1 * | 11/2003 | Manzak et al. | 73/865.8 |
| 6,762,602 B1 | 7/2004 | Laursen et al. | |
| 2006/0071663 A1 * | 4/2006 | Stanley et al. | 324/323 |
| 2010/0308809 A1 * | 12/2010 | Houldley et al. | 324/220 |

FOREIGN PATENT DOCUMENTS

| | | | |
|---|---|---|---|
| EP | 02541440 | | 1/1988 |
| JP | 63120210 A * | | 5/1988 |
| JP | 08178901 A * | | 7/1996 |
| JP | 10260091 A * | | 9/1998 |

* cited by examiner

*Primary Examiner* — Hezron E Williams
*Assistant Examiner* — Nashmiya Fayyaz
(74) *Attorney, Agent, or Firm* — Potomac Patent Group PLLC

(57) ABSTRACT

An inspection sensor module for an in-line pipe inspection tool has a support for mounting the module on the tool, a finger pivotally attached at one end to the support and pivotally attached at the other end to a sensor block carrying one or more inspection sensors. A first leaf spring extends from the support to the finger to bias the finger outwardly, and a second leaf spring extends from the support to the carrier to bias the sensor block. Biasing sensors are mounted on the leading and trailing edges of the first leaf spring to detect movement of the first leaf spring corresponding to movement of the inspection sensors towards or away from the support.

11 Claims, 2 Drawing Sheets

SENSOR FINGER MODULE FOR A PIPELINE INSPECTION TOOL

BACKGROUND OF THE INVENTION

1. Field of the Invention

The present invention relates to pipeline inspection tools, also known as pipeline pigs, and particularly to sensor finger modules for such pipeline pigs for inspecting the condition of pipelines to determine metal loss, cracking or pipeline distortion.

2. Summary of the Prior Art

It is known to inspect the inside of a pipeline using a pipeline pig which may comprise one or more interconnected vehicles which pass down the pipe. Pipeline inspection vehicles typically comprise a main central body to which sensors or other components are mounted. The vehicles may be equipped with cleaning tools for removing debris and contamination from the wall of the pipeline, and sensors for determining the pipeline integrity.

The pig may be towed along the pipeline, or be fitted with pressure plates which enable propulsion by a difference in pressure across the pressure plate.

Knowledge of pipeline defects is critical in preventing future pipeline failure. Defects of particular importance include cracks, regions of metal loss (due to corrosion for example), and distortions such as dents.

Metal loss and cracking are typically identified using sensors such as magnetic flux sensors and/or ultrasound sensors.

Magnetic flux sensors are particularly effective in determining regions of metal loss in the pipeline wall. Such sensors are used for example in a high resolution inspection sensor ring manufactured by the applicants of the present invention. A plurality of such sensors usually are mounted in mounted on a sensor block which is a sensor finger for pipeline inspection. There will be a plurality of such fingers, usually arranged circumferentially around the pig. Individual sensor fingers are resiliently biased against the pipeline wall using beryllium copper leaf springs so as to provide compliance over portions of the inner wall of varying diameter.

Distortions, on the other hand, are identified in the prior art using a separate tool. Typically, either a 'gauge plate' or a single/multi channel calliper tool are used.

A 'gauge plate' is a plate having a diameter typically ~10% less than that of the pipeline bore. The gauge plate may be mounted on a pipeline inspection or cleaning tool and run along the pipeline. Any dents in the pipeline that reduce the bore radius by greater than 10% register a positive indication by the gauge plate. Unfortunately the technique suffers the problem of false indications when the tool passes round pipeline bends, valves, fittings etc. Such indications can confuse the outcome of the run. Further, there is no knowledge of the location along or around the pipeline of dents greater than 10% of radius, and no knowledge at all of dents less than 10% of radius.

An improvement on the gauge plate technique is the calliper tool. This tool has a plurality of circumferentially spaced callipers. The callipers are individually sprung and biased to engage the inner wall of the pipeline.

The single-channel calliper tool is connected to a single recording channel which records indentations in the pipeline and can determine the maximum bore reduction, indentation and ovality of the pipeline. The calliper tool can also give an indication of the location of these features along the length of the pipeline.

Alternatively, a multichannel calliper tool can be employed, having a number of independently recorded calliper channels. They may be deployed either as separate calliper tools or as separate modules on an inspection tool. They are capable of detecting narrower indentations than the single channel callipers and can report azimuth and bend angles. They are of particular use where repairs to select regions of a pipeline wall (such as the top half of the pipe) are to be performed.

The applicants have performed extensive investigations of pipeline defects and pipeline integrity and discovered that the spatially coincident combination of cracks or metal loss defects together with distortion of the pipeline is a much more dangerous combination of defects than either type of defect alone.

However, in order to determine whether metal loss defects (typically detected by a magnetic flux sensor mounted on a sensor finger) are collocated with distortions (detected for example by a calliper tool), both inspection records must be aligned in terms of distance, girth weld number and orientation to an accuracy of a few centimeters. Inaccuracies in the relatively low-tech calliper tool data leads to time-consuming error correction.

Efficiency of inspection is further reduced, since the maximum speeds of operation of calliper tools are not as high as metal loss inspection tools (designed for high speed gas pipelines).

Therefore, at its most general, the present invention proposes that the resilient biasing of a sensor finger is monitored by at least one suitable biasing sensor which detects movement of the biasing means, and hence the finger, thereby to determine the movement of the inspection sensor and hence detect distortions simultaneously with the sensing of pipe defects.

Thus, the present invention may provide an inspection sensor module for a in-line pipe inspection tool, comprising a support for mounting the module on the tool, a finger pivotally connected to the support, at least one inspection sensor at the end of the finger remote from the support, means for resiliently biasing the finger such as to tend to move the at least one inspection sensor away from the support and at least one biasing sensor for detecting movement of the resilient biasing means corresponding to movement of the at least one inspection sensor towards or away from the support.

Thus, the present invention may be embodied in the known arrangements for supporting inspection sensors, but further modified by the provision of the biasing sensor or sensors.

The support may be a platform mountable on the in-line pipe inspection tool, or may be a wall of that tool. Normally, a plurality of inspection sensor modules will be provided circumferentially around the tool, so that the movement of each inspection sensor towards or away from the support is a radial movement in the pipe.

Thus, as the tool moves along the pipe, the or each finger is biased so that the corresponding sensor(s) abuts against the inner surface of the pipe. In that position, the sensor(s) can monitor the pipe to detect defects therein. However, if a deformation in the pipe wall in encountered, the sensor(s) will move radially to conform to the pipe wall, thus moving the finger against the resilience of its biasing means. The biasing sensor will then detect that movement. Thus, simultaneous measurement of the magnetic characteristics of the pipe and the presence of deformations can be determined.

As in the known inspection sensor arrangements, a plurality of inspection sensors may be mounted in a common block, and that block mounted on the finger. The block may be pivotally attached to the finger, to enable the radially outer surface of the block to be maintained parallel to the pipe wall, and suitable biasing provided to achieve this.

Preferably, the resilient biasing means is one or more leaf springs. Thus, a first leaf spring may bear against the finger to bias the finger, and a second leaf spring may be provided bearing against the sensor block to bias that sensor block against the pipe wall. In such an arrangement, the at least one inspection sensor is preferably mounted on the first leaf spring.

In such an arrangement, it is desirable that the at least one inspection sensor is not affected by expansion or contraction of the leaf spring due to temperature changes. To achieve this, it is possible to provide first and second inspection sensors on the leading and trailing edges of the leaf spring, so that both sensors will experience the same change due to temperature changes, but will experience different changes when the leaf spring is deformed.

Normally, the at least one inspection sensor will be a magnetic flux sensor, although it is possible to mount other sensors on the finger in accordance with the present invention.

The above discussion has illustrated the present invention in terms of an inspection sensor module. A second aspect of the invention may provide an in-line inspection tool having at least one, preferably a plurality, of such inspection sensor modules. Moreover, a third aspect of the present invention may provide a method of monitoring the characteristics of a pipe using such an inspection sensor module. This aspect permits simultaneous measurement of pipe characteristics and pipe deformation.

The present invention thus permits the primary inspection data, such as cracking/metal loss data to be spacially aligned with data representing deformation of the pipe. It thus provides more accurate determination of the pipe characteristics.

BRIEF DESCRIPTION OF THE DRAWINGS

An embodiment of the present invention will now be described with reference to the accompanying drawings, in which.

DETAILED DESCRIPTION

Figure 1:
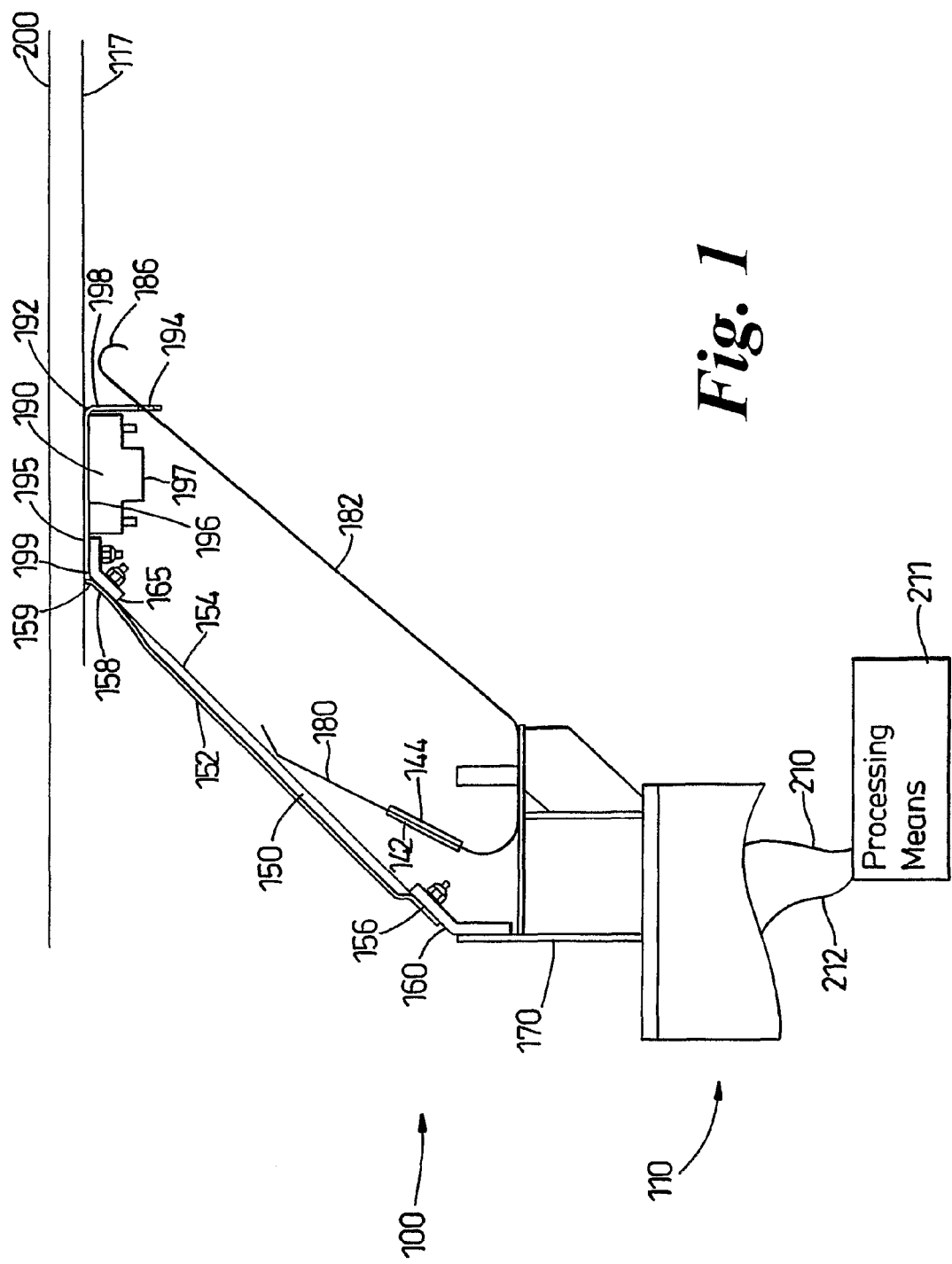
FIG. 1 shows a sensor finger module in a deployed condition in contact with an undistorted portion of a pipeline wall.
Figure 2:
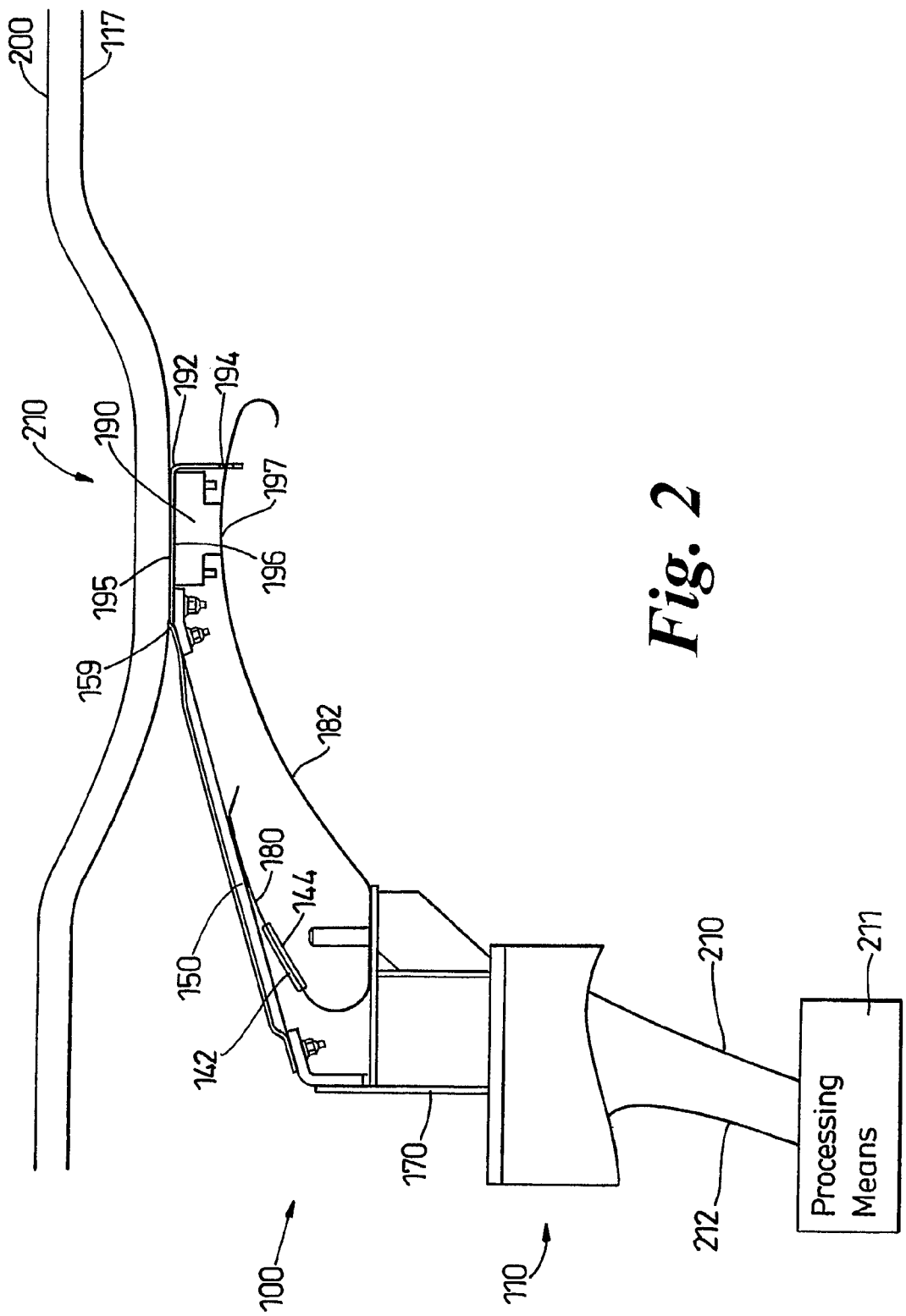
FIG. 2 shows a sensor finger module in a deployed condition in contact with a distorted portion of a pipeline wall corresponding to a dent.

In the embodiment of the present invention shown in FIGS. 1 and 2 an inspection sensor module 100 having a support in the form of a platform support bracket 170 mounted on an inspection tool 110. Although not shown in FIGS. 1 and 2, a plurality of such inspection sensor modules may be provided circumferentially around the inspection tool 110. Thus, FIGS. 1 and 2 illustrate an inspection sensor module 100 extending radially of the inspection tool 110.

The inspection module comprises a sensor 190 mounted on a sensor block 192 proximate a major surface 196 of the sensor block 192, said major surface 196 forming an inspection surface 195 to be maintained in physical contact with the inner wall 117 of a pipeline 200 during pipeline inspection. The sensor block 192 is hinged by a first hinge 165 to a first end 158 of an inspection finger 150, the inspection finger 150 being further hinged by a second hinge 160 at a second end 156 to a platform support bracket 170. The hinges 165, 160 are oriented so as to permit radial deployment of the sensor block 192 relative to the inspection tool 110.

According to this embodiment first and second leaf springs 180, 182 extend from the platform support bracket 170. The first leaf spring 180 contacts the trailing edge 154 of the inspection finger 150 so as to cause the inspection finger 150 assuming a deployed condition. In the deployed condition, the sensor carrier 198 is radially outward of the plane of the platform support bracket 170, and therefore the inspection tool 110 when the platform support bracket 170 is mounted thereupon.

The first leaf spring 180 has two strain gauges 142, 144 located thereupon, a first strain gauge 142 being mounted on the leading edge of the first leaf spring 180 and a second strain gauge 144 being mounted on the trailing edge of the first leaf spring 180. The strain gauges 142, 144 provide data on the deflection of the finger 150; the presence of the gauges on both the leading edge and the trailing edge of the first leaf spring 180 permits temperature compensation of the strain gauge signals.

Those strain gauge signals may pass via a lead 210 to a suitable processing means 211 within the inspection tool 110. Similarly, data from the sensor 190 may pass via a lead 212 to the processing means 211. Thus, the data from the sensor relating to the magnetic characteristics of the pipeline 200 and the data from the strain gauges 142, 144 will be processed, or at least recorded, simultaneously.

The second leaf spring 182 passes behind the sensor 190 and through a spring aperture 194 of the sensor block 192. The spring aperture 194 allows the second leaf spring 182 to slide freely therein so as to allow the sensor carrier 198 to move between deployed and retracted conditions without excessive torque on the sensor carrier 198. It can be seen from FIG. 1 that the action of the first leaf spring 180 causes the hinge 165 to be biased to a position close to the inner wall 117, and the second leaf spring 182 then forces the trailing edge of the sensor carrier 198 against the inner wall 117. Thus, the action of the two leaf springs 180, 182 is to maintain the sensor carrier 198 aligned with the inner wall 117 as the inspection tool 110 moves along the pipeline.

FIG. 2 shows the inspection module 100 in a region 210 of the pipeline 200 having distortion of the pipeline inner wall 117. As can be seen from FIG. 2, when local variations 210 is a deformation in the pipeline 200, the sensor carrier 198 is radially displaced against the bias of the second leaf spring 182, with a corresponding rotation of the inspection arm 150 against the bias of the first leaf spring 180. In a condition of severe deflection of the inspection module 100 such as represented in FIG. 2, the second leaf spring 182 may impinge directly upon a rear surface 197 of the sensor 190. The bias of the second leaf spring 182 is thereby advantageously directed substantially normal to the inspection surface 195.

A free end 186 of the second sensor carrier leaf spring 182 has a bend formed therein so as to prevent retraction of said free end 186 through said spring aperture 194 during pipeline inspection operations.

According to this embodiment the tip of said first end 158 of said inspection finger 150 hinged to said sensor carrier 198 is flared in a direction radially outward so as to form a lip 159. The purpose of the lip 159 is to prevent snag of the leading edge 199 of said sensor carrier 198, against imperfections in the surface morphology of the pipeline inner wall 117 and the inspection surface 195, as well as damage to the inspection sensor module 100.

Thus, when a deformation in the pipeline 200, such as the region 210 in FIG. 2, is encountered, the processing means 211 receives simultaneously data representing the magnetic condition of the region 210, from the sensor 190, and data representing the shape of the region 210 from the strain gauges 142, 144. Thus, the processing means may immediately relate the shape and the magnetic characteristics of the pipe, to prevent any misalignment. Moreover, if the sensor block 192 is deflected so that it is clear of the inner wall 117, due e.g. to the size of the deformation and the speed of movement of the inspection tool, this will be detected by the data from the sensor 190. This will enable any over-measurement in indentations to be detected. Such excessive movement of the sensor block may occur at girth welds, and therefore the present invention avoids mis-measurements due to such welds.

Thus, the present invention permits more accurate determination of the relationship between the magnetic characteristic of the pipeline and the presence or absence of the deformations in the pipeline. It can be achieved by a simple modification of the known finger module arrangements by providing strain gauges on such modules, and passing the data from those strain gauges to the processing circuitry within the inspection tool.

A variety of ways of performing in-line pipeline inspection can be envisaged.

For example, one or more inspection sensor modules mounted on an in-line pipeline inspection tool as described may be introduced to the pipeline environment. The inspection tool is then propelled along the length of pipeline to be inspected. Propulsion may be by towing or by a difference in pressure across a pressure plate attached to the tool.

The output of the inspection sensor and deflection sensor of each inspection sensor module is connected to a monitoring apparatus (e.g. processing means 211) within the inspection tool.

Preferably the monitoring means performs a thermal drift correction of the deflection sensor outputs to obtain a corrected deflection sensor output.

According to the preferred embodiment the monitoring apparatus has recording means for recording the inspection sensor output and the corrected deflection sensor output.

Alternatively, the inspection sensor output and the corrected deflection sensor output may be transmitted by the monitoring apparatus to a remote recording station external to the pipeline. Such transmission may be by wireless communication or via a cable connecting the pig to the remote recording station for recording of the transmitted data.

The invention claimed is:

1. An in-line pipe inspection tool having at least one inspection sensor module, the sensor module comprising:
    a support mounting the module on the tool;
    a finger pivotally connected to the support;
    at least one inspection sensor at the end of the finger remote from the support;
    resilient biasing means for resiliently biasing the finger such as to move the at least one inspection sensor away from the support; and
    at least two biasing sensors for detecting movement of the resilient biasing means corresponding to movement of the at least one inspection sensor towards or away from the support and compensating for a thermal drift of said resilient biasing means,
    wherein the resilient biasing means comprises a first leaf spring and a second leaf spring, and
    wherein at least one of said at least two biasing sensors is configured at a location on a lower portion of a leading edge of said first leaf spring and at least one of said at least two biasing sensors is configured at a location on a lower portion of a trailing edge of said first leaf spring with said leading edge and said trailing edge respective to an operational direction of movement of said pipe inspection tool, wherein said locations of said at least two biasing sensors are adjacent; and
    further wherein the at least one inspection sensor and at least two biasing sensors simultaneously monitor the magnetic and distortion characteristics of a pipe.

2. A pipe inspection tool according to claim 1 having a plurality of inspection sensors mounted in a common block said block being mounted on said finger.

3. A pipe inspection tool according to claim 2, wherein said block is pivotally mounted on said finger.

4. A pipe inspection tool according to claim 2, wherein the resilient biasing means comprises the first leaf spring to bias the finger and the second leaf spring bearing against the sensor block.

5. An in-line pipe inspection tool according to claim 1, wherein said support is a platform mounted on said tool.

6. An in-line pipe inspection tool according to claim 1, having a plurality of inspection sensor modules provided circumferentially around said tool.

7. A method of using an in-line pipe inspection tool to simultaneously monitor the magnetic and distortion characteristics of a pipe, the in-line pipe inspection tool having at least one inspection sensor module, the sensor module comprising a support mounting the module on the tool, a finger pivotally connected to the support, at least one inspection sensor at the end of the finger remote from the support, and means for resiliently biasing the finger such as to tend to move the at least one inspection sensor away from the support, said method comprising:
    configuring at least two biasing sensors for detecting movement of the resilient biasing means corresponding to movement of the at least one inspection sensor towards or away from the support and compensating for a thermal drift of said resilient biasing means,
    wherein the resilient biasing means comprises a first leaf spring and a second leaf spring, and
    wherein at least one of said at least two biasing sensors is configured at a location on a lower portion of a leading edge of said first leaf spring and at least one of said at least two biasing sensors is configured at a location on a lower portion of a trailing edge of said first leaf spring with said leading edge and said trailing edge respective to an operational direction of movement of said pipe inspection tool, wherein said locations of said at least two biasing sensors are adjacent.

8. The method of claim 7, wherein the inspection data collected from said inspection sensor module and representing defects in said pipe is transmitted by a monitoring apparatus to a remote recording station external to said pipe.

9. The method of claim 8, wherein the movement data from said at least two biasing sensors and representing deformations in said pipe is transmitted by a monitoring apparatus to a remote recording station external to said pipe.

10. The method of claim 9, further comprising spatially aligning said inspection data and said movement data for determining locations in said pipe where defects and deformations occur at the same location.

11. The method of claim 8 wherein said defects further comprise cracking in said pipe and material loss in said pipe.

* * * * *